(12) United States Patent
Vincent

(10) Patent No.: US 8,367,369 B2
(45) Date of Patent: Feb. 5, 2013

(54) METHOD AND APPARATUS FOR DETECTING PHYCOCYANIN-PIGMENTED ALGAE AND BACTERIA FROM REFLECTED LIGHT

(75) Inventor: Robert Vincent, Bowling Green, OH (US)

(73) Assignee: Bowling Green State University, Bowling Green, OH (US)

( * ) Notice: Subject to any disclaimer, the term of this patent is extended or adjusted under 35 U.S.C. 154(b) by 927 days.

(21) Appl. No.: 11/499,288

(22) Filed: Aug. 4, 2006

(65) Prior Publication Data

US 2007/0111275 A1    May 17, 2007

Related U.S. Application Data

(62) Division of application No. 10/763,138, filed on Jan. 22, 2004, now Pat. No. 7,132,254.

(51) Int. Cl.
*C12Q 1/02* (2006.01)
(52) U.S. Cl. ........................................ 435/29; 435/173.1
(58) Field of Classification Search .................. None
See application file for complete search history.

(56) References Cited

PUBLICATIONS

Schalles, JF et al. Remote detection and seasonal patterns of phycocyanin, carotenoid and chlorophyll pigments in eutrophic waters. Advances in Limnology. 2000. 55: 153-168.*
Gitelson, AA et al. Optical properties of dense algal cultures outdoors and their application to remote estimation of biomass and pigment concentration in *Spirulina plantensis* (cyanobacteria). J. Phycol. 1995. 31: 828-834.*
Richardson, LL. Remote sensing of algal bloom dynamics. Bioscience. Jul./Aug. 1996. 46(7): 492-501.*
Development and Spatial Distribution of an Algal Bloom in The Dead Sea: A Remote Sensing Study; Aquatic Microbial Ecology, (1997), Oren, A, et al., vol. 13: 219-223.
Phycocyanin Detection From Landsat TM Data for Mapping Cyanobacterial Blooms in Lake Erie; Remote Sensing of Environment, (2004), Vincent, R., et al., vol. 89: 381-392.

* cited by examiner

*Primary Examiner* — Allison Ford
*Assistant Examiner* — Susan E Fernandez
(74) *Attorney, Agent, or Firm* — Marshall & Melhorn, LLC

(57) ABSTRACT

The present invention relates to a method of detecting phycocyanin algae or bacteria in water from reflected light, and also includes devices for the measurement, calculation and transmission of data relating to that method.

13 Claims, 14 Drawing Sheets

Figure 1. LANDSAT 7 ETM+ image (bands 1, 2, and 3 displayed as blue, green, and red, respectively) of part of the July 1, 2000, Path 20 Row 31 frame, showing collection sites of 30 water samples as black dots in Maumee Bay, Ohio. North is to toward the top.

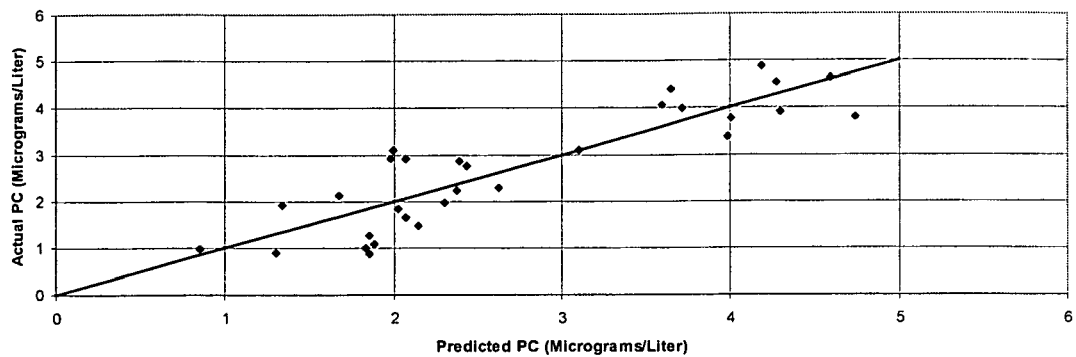

Figure 2. Each diamond represents the actual and predicted value of relative phycocyanin concentration (PC), according to the best model derived from dark-object-subtracted single bands of LANDSAT TM imagery for Lake Erie water samples collected on the same date as the LANDSAT 7 overpass (July 1, 2000). The solid line represents perfect agreement between actual and predicted PC values.

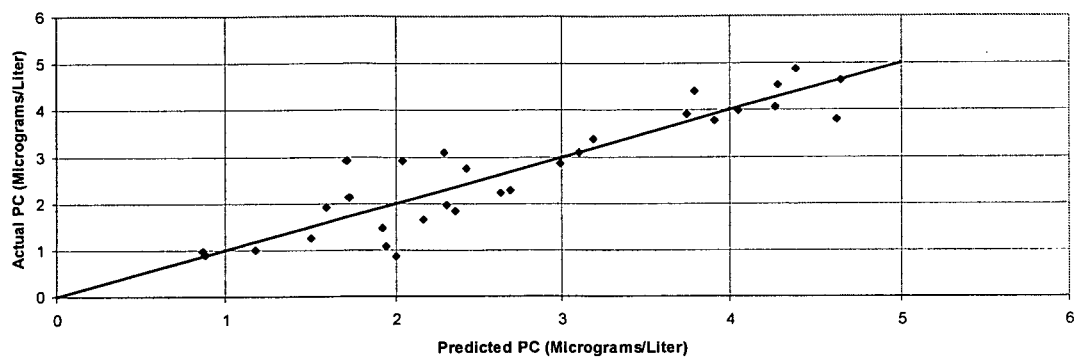

Figure 3. Each diamond represents the actual and predicted value of relative phycocyanin concentration (PC), according to the best model derived from dark-object-subtracted spectral ratios of LANDSAT TM data for Lake Erie water samples collected on the same date as the LANDSAT 7 overpass (July 1, 2000). The solid line represents perfect agreement between actual and predicted PC values.

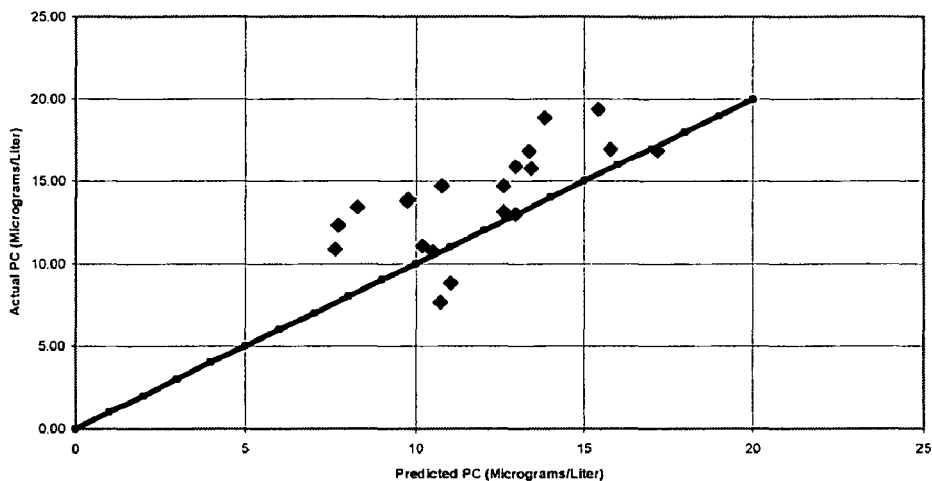
Figure 4. Application of the best LANDSAT 7, July 1, 2000 spectral ratio model for relative phycocyanin concentration (PC) to the LANDSAT 5 dataset (September 27, 2000). Each diamond represents the actual (from the water samples collected on September 27, 2000) and predicted values of relative phycocyanin concentration (PC).

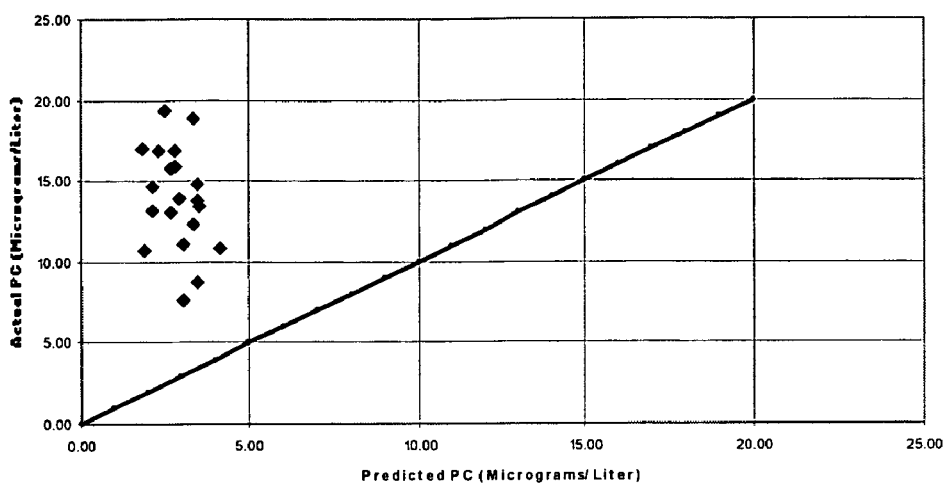
Figure 5. Application of the best LANDSAT 7, July 1, 2000 single band model for relative phycocyanin concentration (PC) to the LANDSAT 5 dataset (September 27, 2000). Each diamond represents the actual (from the water samples collected on September 27, 2000) and predicted values of relative phycocyanin concentration (PC).

Figure 6. Relative phycocyanin content (PC) displayed as red (8.06-9.25 µg/l) to blue (0-5.17 µg/l), from the July 1, 2000 best spectral ratio model, applied to the July 1, 2000, LANDSAT 7 frame. North is toward the top; the whole frame (shown within the black border) covers 185km x185 km on the ground.

Figure 7. Phycocyanin content (PC) displayed as red (10.31-15.77 µg/l) to blue (0-2.50 µg/l), from the July 1, 2000 best spectral ratio model, applied to the September 27, 2000, LANDSAT 5 frame. North is toward the top.

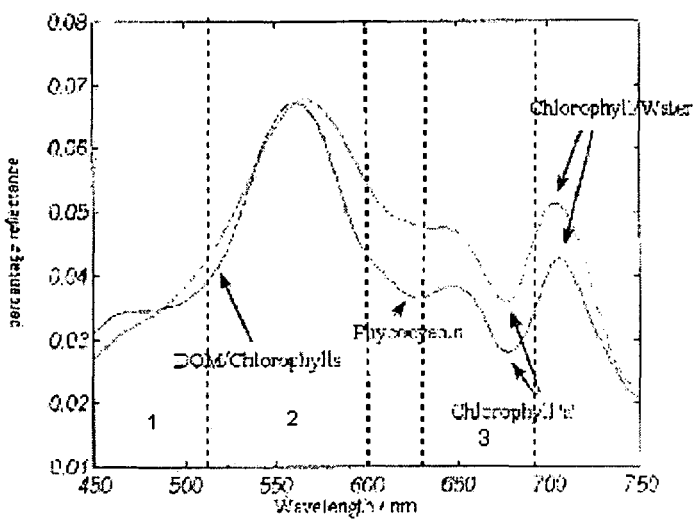

Figure 8. Percent reflectance (%) versus wavelength (nanometers) of absorption features of lake water containing primarily chlorophyll a (top curve) and water from another lake containing both phycocyanin and chlorophyll a (after Green, 2003). Wavelength limits of LANDSAT TM bands 1 (450-520 nm), 2 (520-600 nm), and 3 (630-690 nm) are shown as vertical bars, but limits for TM bands 4 (760-900 nm), 5 (1,550-1,750 nm), and 7 (2,080-2,350 nm) are not shown. Spectral locations of absorption bands for chlorophyll a, phycocyanin, and dissolved organic matter (DOM)/chlorophylls are identified.

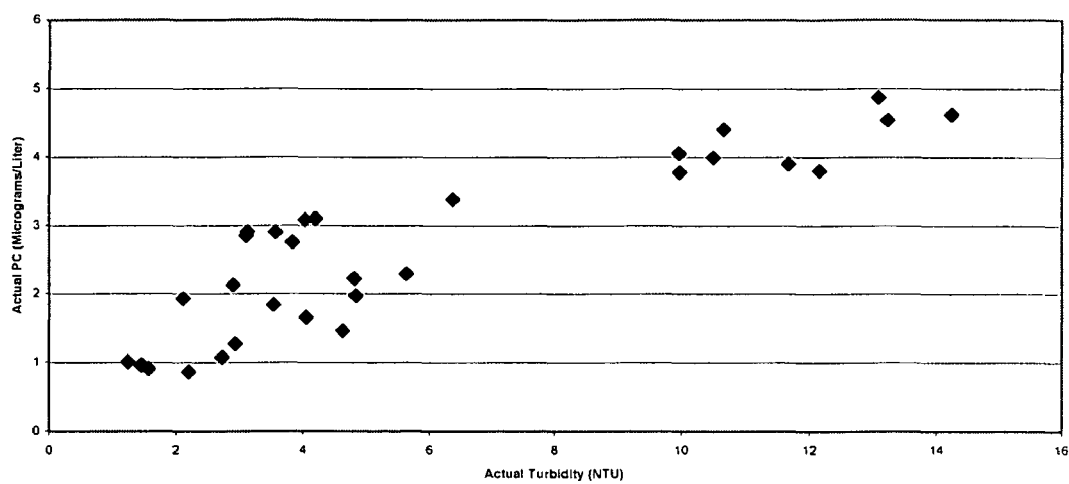
Figure 9. Actual turbidity plotted versus actual PC for the July 1, 2000 water samples.

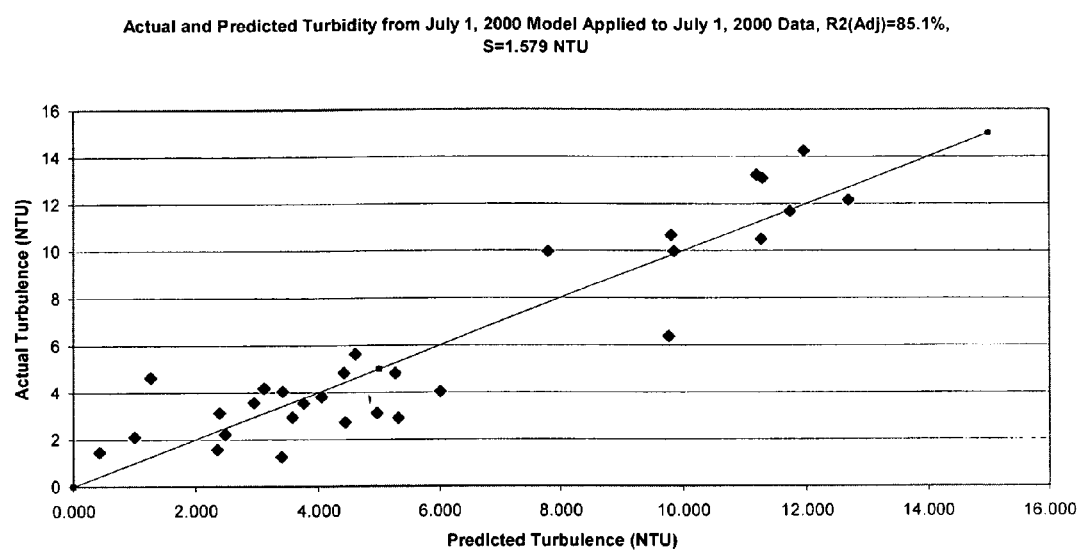
Figure 10. Actual vs. predicted turbidity from the July 1, 2000 turbidity model, applied to the July 1, 2000 LANDSAT 7 frame for P20R31.

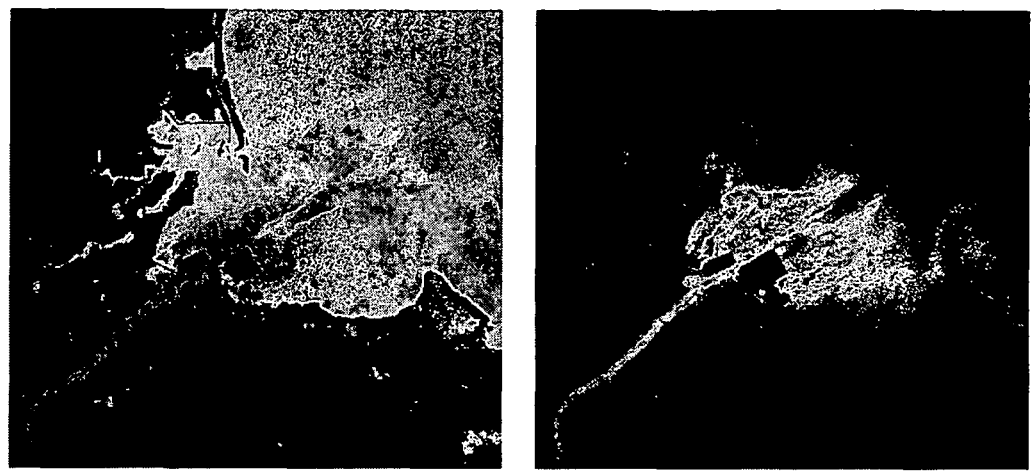
Figure 11. Turbidity (left) and PC (right) images of the Maumee River Mouth subregion (SW corner of Lake Erie) of the July 1, 2000 LANDSAT 7 ETM+ frame. In both cases, red corresponds to the highest contents of the parameter being imaged. North is toward the top.

Figure 12. Phycocyanin content of P19R31 of Western Lake Erie (red is highest PC, from 4.98-12.00 µg/L) for LANDSAT 7 ETM data of July 16, 2002, according to the July 1, 2000 model. North is toward the top.

Figure 13. Phycocyanin content of P19R31 of Western Lake Erie (red is highest PC, from 4.98-12.00 µg/L, and dark blue is zero) for LANDSAT 7 ETM data of August 1, 2002, according to the July 1, 2000 model. North is toward the top.

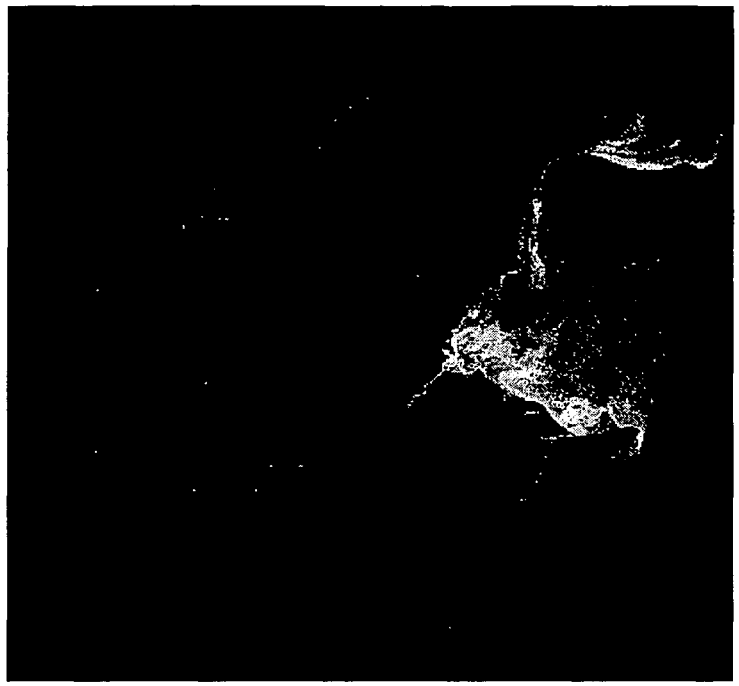
Figure 14. Phycocyanin content of P20R31 of westernmost Lake Erie (red is highest PC, from 11.57-12.51 µg/L, and dark blue is lowest PC, 0.00-5.62 µg/L) for LANDSAT 7 ETM data of August 8, 2002, according to the July 1, 2000 model.

METHOD AND APPARATUS FOR DETECTING PHYCOCYANIN-PIGMENTED ALGAE AND BACTERIA FROM REFLECTED LIGHT

This application is a divisional of U.S. application Ser. No. 10/763,138 filed Jan. 22, 2004, now U.S. Pat. No. 7,132,254, which is incorporated herein by reference.

STATEMENT REGARDING GOVERNMENTAL INTEREST

The present invention was made through funding from grant number NAG3-2629 from the National Aeronautical and Space Administration (NASA) to through the Ohio Aerospace Institute (OAI) as fiduciary agent. The United States Government has certain rights in the invention.

BACKGROUND OF THE INVENTION

The present invention relates to a method of detecting phycocyanin-pigmented algae or bacteria (cyanobacteria) in water from reflected light. These organisms are generally referred to as phycocyanins and cyanobacteria.

In many instances it is desirable to be able to detect the presence microorganisms in water, particularly bodies of water that serve as a source for drinking water or that may serve as a site for recreation, such as for swimming boating, water sports and fishing. Many of these organisms in high concentrations can be harmful to the public and to the environment generally.

It is particularly desirable to be able to be able to detect the presence of microorganisms in water in a manner that is convenient and provides relatively immediate results so that the public may be warned or other actions taken to avoid or eliminate contamination of the assayed water.

The Laurentian Great Lakes have experienced toxin-producing blooms of the cyanobacterium *Microcystis* sp. on a number of occasions over the past decade, including a massive bloom in Lake Erie in 1995 that caused a variety of water quality problems and attracted broad public concerns (Taylor, 1997; Brittain et al, 2000; Budd et al, 2002).

Most freshwater systems in the world are affected by anthropogenic eutrophication, leading to undesirable increases in planktonic and benthic biomass. These phenomena often show large local differences and interactions with patterns of water flow. Among various problems, the amount and distribution of nuisance-forming cyanobacteria is of primary concern for water management. Cyanobacterial blooms may cause a variety of water quality problems, including dissolved oxygen depletion and subsequent fish kills, aesthetic nuisances (e.g., odors, scums, fish tainting, unsightliness), and unpalatable and possibly unsafe drinking water (Carmichael, 2001). Such problems can severely limit aquatic habitat, recreational activities, fisheries, and use of a water body as a potable water resource. *Microcystis* spp., a common bloom-forming species of cyanobacteria, was regularly documented in Lake Erie several decades ago, when the lake was heavily eutrophied as a result of anthropogenic activities (Makarewicz, 1993). Subsequent phosphorus abatement strategies initiated as part of the Great Lakes Water Quality Agreement have been largely successful resulting in a reduction in algal biomass and greater lake transparency. Despite these actions, blooms of *Microcystis* spp. have returned to Lake Erie, recurring each summer since 1995. The return of the blooms appears to coincide with the spread of invasive zebra mussels throughout Lake Erie and is possibly related to selective filtration of other phytoplankton by the mussels and rejection of *Microcystis* spp (Vanderploeg et al. 2001). During September, 1995, Lake Erie experienced a *Microcystis* spp. bloom resembling a thick slick of grass-green paint that extended over the entire surface of the western basin (Taylor, 1997; Brittain et al, 2000; Budd et al, 2002). Another notable bloom was reported in September, 1998 (Lake Erie LaMP, 2000). These blooms are of special concern because at least some Lake Erie strains of *Microcystis* spp. produce the peptide hepatotoxin microcystin, which is harmful to waterfowl or other animals that might drink the untreated water (Brittain et al, 2000). Microcystin has also been identified as a tumor promoter, making long-term ingestion of even low levels of the toxin of concern (Falconer and Humpage, 1996; Carmichael, 2001).

It would be of economic and public health value to be able to detect early stage (emergent) blooms of cyanobacteria, and *Microcystis* spp. in particular, especially if it is on a sufficiently timely basis for municipalities and recreation facilities to implement a response plan. It has been shown that remote sensing technology can be used to estimate the concentration and distribution of cyanobacteria through measuring the concentration of the pigment phycocyanin (Dekker, 1993), which is indicative of the presence of cyanobacteria. In waters off the southeastern coastal U.S. and the Gulf of Mexico, Subramaniam et al (2001) have applied a multispectral classification algorithm that employs data from the Sea-viewing Wide Field-of-View Sensor (SeaWiFS) for mapping blooms of *Trichodesmium* spp., a marine cyanobacterium. In cyanobacteria, phycobiliproteins constitute the major photosynthetic accessory pigments (MacColl and Guard-Friar, 1987). Whereas in marine species the pink-colored phycoerythrin is the dominant accessory pigment, in fresh water taxa, such as *Microcystis* spp., phycocyanin is the dominant pigment (MacColl and Guard-Friar, 1987). With the availability of LANDSAT 7 imagery for every 16-day overpass period, the present invention is intended to develop a LANDSAT TM algorithm for detecting various levels of phycocyanin in western Lake Erie. The present invention also allows for the mapping of turbidity in Lake Erie and its tributaries, to investigate relationships between phycocyanin and turbidity.

With the availability of LANDSAT Thematic Mapper (TM) imagery featuring an overpass cycle of every 16 days (8-day intervals, if both LANDSAT 5 and 7 are employed), one goal of the present invention was to develop a set of algorithms, methods of their use and devices for detecting cyanobacterial blooms in Lake Erie, based on a unique spectral signature produced by phycocyanin, a light-harvesting pigment complex ubiquitous among cyanophytes.

In addition to the features mentioned above, objects and advantages of the present invention will be readily apparent upon a reading of the following description and through practice of the present invention.

SUMMARY OF THE INVENTION

In general terms, the present invention includes a method of determining the presence of phycocyanin algae or bacteria in water as well as a measurement method followed by transmission of data to a remote processing site.

The invention includes a method of determining the presence of phycocyanin algae or bacteria in water from light reflected therefrom. The method comprises the steps of: (a) obtaining a measurement of reflected light from the water, the measurement comprising a measurement of the respective amount of light in at least two, preferably five frequency ranges; and (b) relating the approximate amount of the phycocyanin in the water to the respective amounts of light by applying an algorithm relating the respective amounts of light in the at least two, preferably five frequency ranges to the amount of phycocyanin algae or bacteria in the water. This may be expressed in colonies per milliliter or otherwise through appropriate adjustment of the magnitude and dimensions of the algorithms described herein or generated by the present method. It will be understood that the expression of the amount of phycocyanins in terms of colonies per ml water is only one of several ways to express the amount, and that reference to mathematical equivalents refers to any mathematically or logically related algorithms or expressions.

In a preferred embodiment, the measurement of reflected light from the water comprises the measurement of the respective amount of light in at least five frequency ranges: (i) from about 0.45 µm to about 0.52 µm (ii) from about 0.63 µm to about 0.69 µm; (iii) from about 0.76 µm to about 0.90 µm; (iv) from about 1.55 µm to about 1.75 µm and (v) from about 2.08 µm to about 2.35 µm; and (b) relating the approximate amount of the phycocyanin in the water to the respective amounts of light by applying an algorithm relating the respective amounts of light in the at least five frequency ranges to the amount of phycocyanin algae or bacteria in the water.

Preferably, the measurement of the amount of light in the at least five frequency ranges comprises the measurement, respectively, of: (i) LANDSAT Thematic Mapper ("TM") band 1, (ii) LANDSAT TM band 3, (iii) LANDSAT TM band 4, (iv) LANDSAT TM band 5 and (v) LANDSAT TM band 7. The algorithm may be any algorithm selected from the group consisting of: $X \approx K_1 - K_2 \times (R31) + K_3 \times (R41) - K_4 \times (R43) - K_5 \times (R53) + K_6 \times (R73) - K_7 \times (R74)$ and equivalents wherein:

X is the approximate amount of phycocyanin algae or bacteria expressed in micrograms per liter;

$K_1$ is a value in the range of from about 30 to about 60;

$K_2$ is a value in the range of from about 5 to about 15;

$K_3$ is a value in the range of from about 20 to about 35;

$K_4$ is a value in the range of from about 100 to about 130;

$K_5$ is a value in the range of from about 3 to about 10;

$K_6$ is a value in the range of from about 30 to about 50;

$K_7$ is a value in the range of from about 5 to about 20;

R31 is the value of LANDSAT TM band 3 divided by LANDSAT TM band 1, after subtraction for atmospheric haze separately in each band;

R41 is the value of LANDSAT TM band 4 divided by LANDSAT TM band 1, after subtraction for atmospheric haze separately in each band;

R43 is the value of LANDSAT TM band 4 divided by LANDSAT TM band 3, after subtraction for atmospheric haze separately in each band;

R53 is the value of LANDSAT TM band 5 divided by LANDSAT TM band 3, after subtraction for atmospheric haze separately in each band;

R73 is the value of LANDSAT TM band 7 divided by LANDSAT TM band 3, after subtraction for atmospheric haze separately in each band; and R74 is the value of LANDSAT TM band 7 divided by LANDSAT TM band 4, after subtraction for atmospheric haze separately in each band.

Preferably, the K values are as follows:

$K_1$ is a value in the range of from about 45 to about 50;

$K_2$ is a value in the range of from about 7 to about 11;

$K_3$ is a value in the range of from about 25 to about 35;

$K_4$ is a value in the range of from about 110 to about 120;

$K_5$ is a value in the range of from about 5 to about 8;

$K_6$ is a value in the range of from about 35 to about 45; and $K_7$ is a value in the range of from about 10 to about 15.

Most preferably the K values are as follows:

$K_1$ is a value in the range of from about 46 to about 48;

$K_2$ is a value in the range of from about 8 to about 10;

$K_3$ is a value in the range of from about 27 to about 30;

$K_4$ is a value in the range of from about 115 to about 120;

$K_5$ is a value in the range of from about 6 to about 8;

$K_6$ is a value in the range of from about 38 to about 43; and $K_7$ is a value in the range of from about 13 to about 15.

The method according to the present invention is such that the calculated value of phycocyanin-pigmented algae or bacteria (X) correlates to the actual measured amount of the phycocyanin in the water by an adjusted square correlation value (i.e., $R^2$ adjusted) in excess of 60% and as high as in excess of 70%.

The present invention may additionally comprise the step of generating a report of the approximate amount of the phycocyanin-pigmented species in the water. This may be done using electronics adapted to digitize and process the data using an appropriate algorithm, such as that described herein. For instance, the report may include an estimate of the number of the phycocyanin colonies per ml in the water.

The method of the present invention may also include the step of transmitting data relating to the approximate amount of the phycocyanin in the water to a site remote from the site where the measurement takes place. This may be done using any transmission method including land line or wireless transmission. This is also used advantageously where the reflected light is sensed remotely by aircraft, satellite, boat or buoy. Processing of the data may take place at the site of light uptake or may be carried out at a remote location after transmission of the raw data. The estimated phycocyanin report may be sent to public authorities, such as police departments, fire and rescue departments or life guard services to warn swimmers, boaters, sportsman or the public at large that a given body of water, or portion thereof, likely contains elevated/dangerous levels of phycocyanin algae or bacteria.

The invention also includes an apparatus for determining the presence of phycocyanin algae or bacteria in water from light reflected therefrom, the device comprising: (a) a measurement device adapted to measure reflected light from the water, the measurement comprising a measurement of the respective amount of light in at least five frequency ranges: (i) from about 0.45 µm to about 0.52 µm; (ii) from about 0.63 µm to about 0.69 µm; (iii) from about 0.76 µm to about 0.90 µm; (iv) from about 1.55 µm to about 1.75 µm; and (v) from about 2.08 µm to about 2.35 µm; and (b) a processor capable of relating the approximate amount of the phycocyanin in the water to the respective amounts of light by applying an algorithm relating the respective amounts of light in the at least five frequency ranges to the amount of phycocyanin algae or bacteria in the water.

Most preferably, the at least five frequency ranges comprise, respectively: (i) LANDSAT TM band 1, (ii) LANDSAT TM band 3 and (iii) LANDSAT TM band 4, such as (iv) LANDSAT TM band 5, and (v) LANDSAT TM band 7 and wherein the algorithm is any algorithm selected from the group consisting of: $X \approx K_1 - K_2 \times (R31) + K_3 \times (R41) - K_4 \times (R43) - K_5 \times (R53) + K_6 \times (R73) - K_7 \times (R74)$ and equivalents wherein:

X is the approximate amount of phycocyanin algae or bacteria expressed in micrograms per liter;

$K_1$ is a value in the range of from about 30 to about 60;

$K_2$ is a value in the range of from about 5 to about 15;

$K_3$ is a value in the range of from about 20 to about 35;

$K_4$ is a value in the range of from about 100 to about 130;

$K_5$ is a value in the range of from about 3 to about 10;

$K_6$ is a value in the range of from about 30 to about 50;

$K_7$ is a value in the range of from about 5 to about 20;

$R31$ is the value of LANDSAT TM band 3 divided by LANDSAT TM band 1, after subtraction for atmospheric haze separately in each band;

$R41$ is the value of LANDSAT TM band 4 divided by LANDSAT TM band 1, after subtraction for atmospheric haze separately in each band;

$R43$ is the value of LANDSAT TM band 4 divided by LANDSAT TM band 3, after subtraction for atmospheric haze separately in each band;

$R53$ is the value of LANDSAT TM band 5 divided by LANDSAT TM band 3, after subtraction for atmospheric haze separately in each band;

$R73$ is the value of LANDSAT TM band 7 divided by LANDSAT TM band 3, after subtraction for atmospheric haze separately in each band; and $R74$ is the value of LANDSAT TM band 7 divided by LANDSAT TM band 4, after subtraction for atmospheric haze separately in each band.

Preferably, the K values are as follows:

$K_1$ is a value in the range of from about 45 to about 50;
$K_2$ is a value in the range of from about 7 to about 11;
$K_3$ is a value in the range of from about 25 to about 35;
$K_4$ is a value in the range of from about 110 to about 120;
$K_5$ is a value in the range of from about 5 to about 8;
$K_6$ is a value in the range of from about 35 to about 45; and
$K_7$ is a value in the range of from about 10 to about 15.

Most preferably the K values are as follows:

$K_1$ is a value in the range of from about 46 to about 48;
$K_2$ is a value in the range of from about 8 to about 10;
$K_3$ is a value in the range of from about 27 to about 30;
$K_4$ is a value in the range of from about 115 to about 120;
$K_5$ is a value in the range of from about 6 to about 8;
$K_6$ is a value in the range of from about 38 to about 43; and
$K_7$ is a value in the range of from about 13 to about 15.

It is preferred that the apparatus is capable of performing such that the calculated value of phycocyanin correlates to the actual measured amount of the phycocyanin in the water by a correlation value in excess of 60, and most preferably by a correlation value in excess of 70.

The apparatus may additionally include a report generator adapted to generate a report of said approximate amount of said phycocyanin in the water. Such a report generator may be any device that is adapted to place the data into a tangible medium, such as a printer, CD burner, flash memory, magnetic storage media, etc.

The apparatus may additionally include a transmitter adapted to transmit data relating to the approximate amount of the phycocyanin in the water from the processor to a site remote from the site where the measurement takes place. Such a transmitter may include those adapted to send data such as through land line or wireless transmission, including telephone, internet, cell phone, radio and the like.

The measurement device may be any device adapted to sense and record and/or transmit the light frequencies described above. Examples include photosensors, cameras, digital cameras and video cameras, etc.

The processor may be any data processing device having programming instructions for applying the algorithm, such as preferably a microprocessor.

It is preferred that the algorithm comprises a linear relationship between the approximate amount of the phycocyanin in the water and sum of (a) the ratio of the first frequency to the second frequency and (b) the ratio of the second frequency to the third frequency.

The measurement device may be placed in any position from which it can sense the required light frequencies, such as on a buoy, a boat, a light house or similar dedicated tower structure, an elevated lifeguard house. The measurement device may also be in the form of a handheld device, such as a camera connected to a processor for processing the recorded light frequencies, the device may also be in the form of a device similar to a personal digital assistant with light recording and processing functions.

Another variation of the invention is a system using transmission of light measurement data to processor at a different location, recognizing that the processing may be done at a different location than the light sensing/recording.

In general terms, this variation is a system for determining the presence of phycocyanin algae or bacteria in water from light reflected therefrom, the device comprising (a) a measurement device adapted to measure reflected light from the water, the measurement comprising a measurement of the respective amount of light in at least five frequency ranges: (i) from about 0.45 μm to about 0.52 μm; (ii) from about 0.63 μm to about 0.69 μm; (iii) from about 0.76 μm to about 0.90 μm; (iv) from about 1.55 μm to about 1.75 μm; and (v) from about 2.08 μm to about 2.35 μm; and (b) a processor at the remote site and capable of relating the approximate amount of the phycocyanin in the water to the respective amounts of light by applying an algorithm relating the respective amounts of light in the at least five frequency ranges to the amount of phycocyanin algae or bacteria in the water.

The invention also includes a method of developing an apparatus for determining the presence of phycocyanin algae or bacteria in water from light reflected therefrom, the device comprising (a) obtaining a measurement of reflected light from the water, the measurement comprising a measurement of the respective amount of light of at least two frequencies; (b) developing an algorithm relating the respective amounts of light in the at least two frequencies to the amount of phycocyanin algae or bacteria in the water through linear regression analysis; (c) producing a processor capable of relating the approximate amount of the phycocyanin in the water to the respective amounts of light by applying an algorithm relating the respective amounts of light in the at least five frequency ranges to the amount of phycocyanin algae or bacteria in the water; and (d) providing a measurement device adapted to measure reflected light from the water and adapted to provide data relating to the measurement to the processor.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

Novel features and advantages of the present invention, in addition to those mentioned above, will become apparent to those skilled in the art from a reading of the following detailed description in conjunction with the accompanying drawings summarized as follows:

FIG. 1 is a LANDSAT 7 ETM+ image (bands 1, 2, and 3 displayed as blue, green, and red, respectively) of part of the Jul. 1, 2000, Path 20 Row 31 frame, showing collection sites of 30 water samples as black dots in Maumee Bay, Ohio. North is to toward the top, as taken in accordance with one embodiment of the present invention;

FIG. 2 is a graph of actual and predicted values of relative phycocyanin concentration (PC), according to the best model derived from dark-object-subtracted single bands of LANDSAT TM imagery for Lake Erie water samples collected on the same date as the LANDSAT 7 overpass (Jul. 1, 2000), in accordance with one embodiment of the present invention;

FIG. 3 is a graph of actual and predicted value of relative phycocyanin concentration (PC), according to the best model derived from dark-object-subtracted spectral ratios of LANDSAT TM data for Lake Erie water samples collected on the same date as the LANDSAT 7 overpass (Jul. 1, 2000), in accordance with one embodiment of the present invention;

FIG. 4 is a graph of actual (from the water samples collected on Sep. 27, 2000) and predicted values of relative phycocyanin concentration (PC) showing application of the best LANDSAT 7, Jul. 1, 2000 spectral ratio model for relative phycocyanin concentration (PC) to the LANDSAT 5 dataset (Sep. 27, 2000), in accordance with one embodiment of the present invention;

FIG. 5 is a graph of actual (from the water samples collected on Sep. 27, 2000) and predicted values of relative phycocyanin concentration (PC) showing application of the best LANDSAT 7, Jul. 1, 2000 single band model for relative phycocyanin concentration (PC) to the LANDSAT 5 dataset (Sep. 27, 2000), in accordance with one embodiment of the present invention;

FIG. 6 is a graph of relative phycocyanin content (PC) displayed as red (8.06-9.25 µg/l) to blue (0-5.17 µg/l), from the Jul. 1, 2000 best spectral ratio model, applied to the Jul. 1, 2000, LANDSAT 7 frame, in accordance with one embodiment of the present invention;

FIG. 7 is a photograph illustrating phycocyanin content (PC) displayed as red (10.31-15.77 µg/l) to blue (0-2.50 µg/l), from the Jul. 1, 2000 best spectral ratio model, applied to the Sep. 27, 2000, LANDSAT 5 frame, in accordance with one embodiment of the present invention;

FIG. 8 is a graph of percent reflectance (%) versus wavelength (nanometers) of absorption features of lake water containing primarily chlorophyll a (top curve) and water from another lake containing both phycocyanin and chlorophyll a (after Green, 2003). Wavelength limits of LANDSAT TM bands 1 (450-520 nm), 2 (520-600 nm), and 3 (630-690 nm) are shown as vertical bars, but limits for TM bands 4 (760-900 nm), 5 (1,550-1,750 nm), and 7 (2,080-2,350 nm) are not shown. Spectral locations of absorption bands for chlorophyll a, phycocyanin, and dissolved organic matter (DOM)/chlorophylls are identified, in accordance with one embodiment of the present invention;

FIG. 9 is a graph of actual turbidity plotted versus actual PC for the Jul. 1, 2000 water samples, in accordance with one embodiment of the present invention;

FIG. 10 is a graph of actual vs. predicted turbidity from the Jul. 1, 2000 turbidity model, applied to the Jul. 1, 2000 LANDSAT 7 frame for P20R31, in accordance with one embodiment of the present invention;

FIG. 11 is a photograph illustrating turbidity (left) and PC (right) images of the Maumee River Mouth subregion (SW corner of Lake Erie) of the Jul. 1, 2000 LANDSAT 7 ETM+ frame), in accordance with one embodiment of the present invention;

FIG. 12 is a photograph illustrating phycocyanin content of P19R31 of Western Lake Erie (red is highest PC, from 4.98-12.00 µg/L) for LANDSAT 7 ETM data of Jul. 16, 2002, according to the Jul. 1, 2000 model, in accordance with one embodiment of the present invention;

FIG. 13 is a photograph illustrating phycocyanin content of P19R31 of Western Lake Erie (red is highest PC, from 4.98-12.00 µg/L, and dark blue is zero) for LANDSAT 7 ETM data of Aug. 1, 2002, according to the Jul. 1, 2000 model, in accordance with one embodiment of the present invention; and FIG. 14 is a photograph illustrating Phycocyanin content of P20R31 of westernmost Lake Erie (red is highest PC, from 11.57-12.51 µg/L, and dark blue is lowest PC, 0.00-5.62 µg/L) for LANDSAT 7 ETM data of Aug. 8, 2002, according to the Jul. 1, 2000 model, in accordance with one embodiment of the present invention.

DETAIL DESCRIPTION OF PREFERRED EMBODIMENT(S)

The preferred system herein described is not intended to be exhaustive or to limit the invention to the precise forms disclosed. They are chosen and described to explain the principles of the invention and the application of the method to practical uses so that others skilled in the art may practice the invention.

The present invention includes the use of algorithms developed from LANDSAT 7 ETM+ data for the Jul. 1, 2000 overpass and LANDSAT 5 TM data for the Sep. 27, 2000 overpass for Path 20 Row 31 (including Toledo, Ohio) to measure relative phycocyanin content (PC) and turbidity in the western basin of Lake Erie. Water samples were collected from discrete hydrographic stations arranged in a 20 km×4 km grid adjacent to the Ohio shoreline during a 6-hour period spanning each of the two LANDSAT overpasses. The samples were analyzed for Chlorophyll a content and turbidity. In addition, the concentration of phycocyanin, a light-harvesting pigment associated with cyanobacteria, was estimated from the ratio of phycocyanin:chl a in vivo fluorescence (IVPF/IVCF). A dark-object-subtracted, spectral ratio model derived from the Jul. 1, 2000 data was found to be the most robust, when applied to the Sep. 27, 2000 data. The same Jul. 1, 2000 model (or algorithm) for PC was then applied to LANDSAT 7 ETM+ frames for Jul. 16 and Aug. 1, 2002 of the Path 19 Row 31 frame (including Cleveland, Ohio) and to the Aug. 8, 2002 frame of Path 20 Row 31. Moderate, very low, and high PC values were detected in the western basin of Lake Erie on Jul. 16, Aug., 1, and Aug. 8, 2002, respectively. On Sep. 17, 2002, local media reported a large *Microcystis* sp. bloom in the western basin. The high PC values on Aug. 8, 2002 may have been an early detection of the large *Microcystis* sp. bloom that was reported 5 weeks later. The PC algorithm derived in this study will improve our understanding of the temporal and spatial dynamics of cyanobacterial bloom formation in Lake Erie and other systems. It may also serve to alert municipalities to the presence of potentially toxic bloom events by sending relevant data and reporting these results.

The invention also includes a system using an algorithm for converting LANDSAT TM multispectral signals into images showing different values of phycocyanin colonies per milliliter of water. This system and method were tested in Lake Erie and its wider tributaries detect phycocyanin algae in the waters of Lake Erie to analyze the changes in water populations as they may affect human and wildlife activities. By gathering water samples during the period of time the satellite passes over Lake Erie and applying test kits, the level of phycocyanin populations was determined. The preferred algorithm combines 2 ratios of three of the six spectral bands within silicon detector range (one to determine chlorophyll and the other turbidity).

The method of the present invention may be carried out using any sensing appropriate light sensing devices adapted to capture the algorithm-relevant frequencies as described herein, including satellite and surface sensors (such as a wireless multispectral phycocyanin detector, or WIMCOD) for detection of phycocyanin, as well as for phycocyanin pigment, which is found in several types of toxic algae. Phycocyanin is a natural pigment that is not chlorophyll pigment, but which is found in some blue-green algae.

An algorithm that may be used in the present invention, which may be carried out by computer instructions for producing a particular type of image that can be used to map a particular substance from a remote sensing platform in space, in an aircraft, or on the ground, may be determined as follows.

LANDSAT Thematic Mapper (TM) is a sensor that has 8 spectral bands, 6 of which have a 30-meter spatial resolution and which detect visible and infrared radiation (sunlight) reflected off the Earth's surface. The following bands were employed, with the wavelength limits (in micrometers, or µm) of their spectral band-widths given below for the LANDSAT 7 version of TM, called ETM+, and the LANDSAT 4 and 5 versions, called TM:

TABLE 1

TM and ETM+ Spectral Bandwidths
Bandwidth (µ) Full Width - Half Maximum

| Sensor | Band 1 Plot Data | Band 2 Plot Data | Band 3 Plot Data | Band 4 Plot Data | Band 5 Plot Data | Band 6 Plot Data | Band 7 Plot Data | Band 8 Plot Data |
|---|---|---|---|---|---|---|---|---|
| TM | 0.45-0.52 | 0.52-0.60 | 0.63-0.69 | 0.76-0.90 | 1.55-1.75 | 10.4-12.5 | 2.08-2.35 | N/A |
| ETM+ | 0.45-0.52 | 0.53-0.61 | 0.63-0.69 | 0.78-0.90 | 1.55-1.75 | 10.4-12.5 | 2.09-2.35 | .52-.90 |

For instance, band 2 of the LANDSAT 7 version of the TM sensor (called ETM+) has wavelength limits of 0.53-0.61 µm, band 3 has limits of 0.63-0.69 µm, and band 4 has limits of 0.78-0.90 µm. When mapping phycocyanin pigment, phycocyanin algae in Lake Erie and its tributaries with LANDSAT 7 data, it had to be determined which or how many of bands 1-5 and 7 (which have 30-m spatial resolution and relatively narrow spectral bands, as opposed to the 60-m spatial resolution of band 6 and the relatively wide band-width of the 15-m-resolution band 8) to use. A mathematical procedure (multiple regressions) was applied to seek the best combinations of those bands to correlate with the target phycocyanin concentration.

It was determined that the use of the single band radiances (even if they were reduced to spectral reflectances from theoretical atmospheric models) as inputs to this procedure, the resulting algorithm would not be very robust (i.e., repeatable under different solar illumination and atmospheric conditions). Therefore, spectral ratios (ratios of spectral bands, after empirical correction for atmospheric haze through a process referred to as "dark object subtraction," were input to the mathematical procedure for each pixel from which a water sample had been collected. These 15 non-reciprocal ratios (R21, R31, R32, R41, . . . R75) became the dependent variables and phycocyanin became the independent variable, which was the result of lab analysis of the water samples. For the LANDSAT 7 overpass, 30 water samples were collected, which were measured for both phycocyanin and phycocyanin content. The best subsets of spectral ratios were determined, and then the ones with the highest $R^2$ (Adjusted) values were tested to see if they passed the Durbin-Watson test. The model with the highest $R^2$ (Adjusted) that also passed the Durbin-Watson test was the model that was considered to be the best.

The present invention thus takes advantage of two technology-based approaches: the use of remote sensing as a tool to study regional-scale aquatic ecosystem dynamics, and the use of sensitive fluorescence methods to identify and quantify algal pigments. The present invention has potential economic and public health value to municipalities located along the lake because it aims toward measuring the abundance of cyanobacteria on a sufficiently timely basis to allow municipalities and recreation facilities that depend on Lake Erie for drinking water to respond to the threat. The best resulting algorithm was applied to Lake Erie and its tributaries, as well as to some small inland lakes in Northern Ohio, though only Lake Erie results are reported here. It also has potential for assisting future assessment and monitoring of cyanobacteria blooms, water quality, and aquatic ecosystem health in other regions and, perhaps, on a global scale. These results were obtained in a freshwater lake, however, and the algorithm may require changes for use in marine environments.

Powerful remote sensing techniques have become available in the last two decades that facilitate practice of the present invention to determine large-scale biological processes in difficult environments. At least four satellites have been commonly used for chlorophyll and phytoplankton mapping: AVHRR, SEAWIFS, and MODIS, all of which have spatial resolutions that range from 250-1,000 meters in pixel size. Where one is interested in results beyond the Great Lakes, to other fresh water lakes and their tributaries, as well as small inland lakes, the 30-meter resolution of the six visible/reflective IR spectral bands of LANDSAT TM and ETM+ are preferably selected. However, LANDSAT TM data has traditionally had one exceptional disadvantage: though data are collected by the LANDSAT satellites with a 16-day frequency (8-day frequency for two LANDSAT satellites), the data were not readily available to civilian scientists in less than approximately 60 days following the data collection. The availability of LANDSAT TM data within 24-48 hours through the OhioView consortium (a remote sensing consortium of eleven of Ohio's public research universities) permits non-government scientists to perform time-sensitive research with LANDSAT data for the first time since ERTS I (later called LANDSAT I) was orbited in 1972.

An experiment was conducted on Jul. 1, 2000, a day of LANDSAT 7 overpass. Thirty sites with a grid spacing of 2 km over three, 20-km-long lines were surveyed (with GPS coordinates) in Maumee Bay, which is located at the southwestern corner of Lake Erie, with surface water samples collected at each site. FIG. 1 shows a natural color image of Maumee Bay (a small part of the Jul. 1, 2000 LANDSAT ETM+ frame), with the location points of all 30 water samples collected within 3 hours of the overpass, about 30 minutes before noon, EDT. This followed the Presidential Order that permitted the un-fuzzing of the GPS satellites in the U.S. in May, 2000, resulting in precise location data correct to within approximately 3 meters in both Easting and Northing, which is much less than the size of a LANDSAT TM pixel (28.5 m×28.5 m) for the six reflective bands (1-5 and 7). In situ pH value, temperature, and turbidity were also measured at each site. Sampling was also conducted on Sep. 27, 2000, coinciding with a LANDSAT 5 overpass, with 20 sites, but without turbidity data. The data collection sites were only approximately the same as for the first LANDSAT overpass, but GPS measurements were made at each site.

Chlorophyll a retained on a 0.2 μm PCTE filter (GEOsmonics, Minnetonka, Minn.) was determined by fluorometric analysis following extraction in 90% acetone at −20° C. for 24 hours (Welschmeyer 1994) using a TD 700 fluorometer (Turner Designs, Sunnyvale, Calif.). Phycocyanin in vivo fluorescence (IVPF) was measured on samples using narrow-band interference filters (Andover Corp., NH) with excitation at 630±10 nm and emission at 660±10 nm (Watras and Baker, 1988). In vivo Chlorophyll a fluorescence (IVCF) was measured on the same fluorometer, but using a filter set with excitation and emission wavelengths of 430±10 nm and 680±10 nm. In the present invention, one may use the product of the ratio of IVPF/IVCF and extractive chlorophyll a to provide an estimate of the relative concentration of phycocyanin (PC=Relative Phycocyanin Content). PC values are proportional to absolute phycocyanin content. Cultures of *Microcystis aeruginosa* were used as standards to calibrate the fluorometer response for IVPF. Used in this capacity were *M. aeruginosa* UTCC 124, a non-toxic congener from the University of Toronto Culture Collection and *M. aeruginosa* strain LE-3, an isolate from Lake Erie collected during the 1995 bloom (Brittain et al, 2000).

LANDSAT 7 and LANDSAT 5 TM data were processed using the ERMAPPER image processing software package and Minitab statistical software package, both of which are commercially available. Dark object subtraction (Vincent, 1997), which is briefly described below, was applied to each band to reduce the effects of atmospheric haze from time one to time two.

The spectral radiance detected by the ith spectral band sensor can be approximated by the following equation:

$$L_i = \int_{\lambda_{lower}}^{\lambda_{Upper}} (s\alpha'_\lambda \rho_\lambda + \beta'_\lambda) d\lambda \approx \quad \text{(Eqn. 1)}$$
$$(s\alpha'_i \rho_i + \beta'_i)(\lambda_{Upper} - \lambda_{Lower}) = s\alpha_i \rho_i + \beta_i$$

where $L_i$=the spectral radiance detected by the ith spectral band sensor for a given pixel on the Earth's surface.

$\lambda_{Upper}$=upper wavelength limit of ith spectral band.
$\lambda_{Lower}$=lower wavelength limit of ith spectral band.
s=the shadow/slope factor that is 0 for total shadow and 1 for no shadow or slope in that pixel.
$\alpha_i = \alpha'_i(\lambda_{Upper} - \lambda_{Lower})$=wavelength-dependent, multiplicative factor that includes atmospheric transmission and sensor gain averaged over the ith band.
$\rho_i$=spectral reflectance of the Earth's surface averaged over the ith band.
$\beta_i$=wavelength-dependent, additive factor that includes atmospheric haze averaged over the ith band and sensor additive offset.

The approximation in Equation 1 is that the spectral bandwidth is much narrower than the width of most spectral absorption features of the object being observed. This approximation gets increasingly better with narrower spectral band-widths. All of the chemical composition information to be obtained from the surface of the Earth in a given pixel is found in the $\rho_i$ term, and in none of the other terms. Thus, it is desirable to remove the additive term, which can be done simply by histogramming each spectral band and determining the minimum digital number (DN) found in all (or nearly all) of the pixels in the image. One less than this minimum DN is taken to be the value of the $\beta_i$ term (the dark object for the ith spectral band) in Equation 1, which is the same for the entire frame of image data, under clear-sky conditions and a reasonably flat terrain or water surface. When one less than the minimum DN number is taken to be the dark object for a given spectral band, there will be no division by zero when that spectral band is employed as the denominator of a ratio. There is a different dark object for each spectral band, and the magnitude of the dark object is greatest for TM band 1, less for band 2, even less for band 3, and sometimes as low as zero for band 4. Dark objects for TM bands 5 and 7 are usually zero.

Once the dark object is found for the ith band, it is subtracted from all other pixels in the scene, yielding the equation for dark-object-subtracted radiances $L'_i$:

$$L'_i = L_i - \beta_i = s\alpha_i \rho_i \quad \text{Eqn. 2}$$

Although $\alpha_i$ is approximately constant over the whole frame, under the assumed conditions of clear sky and small elevation differences (reasonably flat) throughout the image, both s and $\rho_i$ vary from pixel to pixel. Because s holds no information about the chemical composition of the pixel, it is highly desirable that it should be eliminated, which can be accomplished with a spectral ratio (Vincent, 1997). A spectral ratio, denoted as $R_{i,j}$, is the quotient of the dark-object-subtracted radiances in the ith and jth spectral bands, or $$R_{i,j} = \frac{L'_i}{L'_j} = \frac{s\alpha_i \rho_i}{s\alpha_j \rho_j} = \left(\frac{\alpha_i}{\alpha_j}\right)\left(\frac{\rho_i}{\rho_j}\right) \quad \text{Eqn. 3}$$

Note that the shadow/slope factor is cancelled out, and what is left are two multiplicative terms, the first of which is an atmospheric/multiplicative gain factor that is the same throughout the image, under the assumed conditions. The second term is a ratio of reflectances in the ith and jth bands for the pixel being observed and carries all the information about chemical composition. The spectral ratio of Equation 3 has been demonstrated many times on land to be more robust to solar illumination, atmospheric, and sensor parameter changes than any parameter based on linear combinations of single spectral bands because both $\beta_i$ and s have been removed by the dark-object-corrected ratio process.

$L'_i$ for six single bands of TM and the fifteen non-reciprocal spectral ratios ($R_{i,j}$) that can be produced from those 6 single bands were extracted from the image data for each of the pixels that contained the water sample collection sites for the Jul. 1, 2000 overpass of LANDSAT 7 (30 samples) and the Sep. 27, 2000 overpass of LANDSAT 5 (22 samples). Both types of data (single band combinations and spectral ratio combinations) were used to construct multiple regression models describing the relationship between the LANDSAT TM data and each of the measured values of turbidity, chlorophyll a and the ratio IVPF/IVCF, as well as the relative phycocyanin concentration (PC), which was estimated for each water sample from the product of chlorophyll a content and the IVPF/IVCF ratio.

Moving beyond any pre-conceived notions concerning the best single bands or the best spectral ratios for mapping the parameters of interest (PC and turbidity), the present invention may be arrived at by inputting some or all of them and allowing the multiple regression method sort the best ones out. The best multiple regression models for PC and turbidity were sought separately for linear combinations of single band and linear combinations of spectral ratios. It was our expectation, from Equation 3 and past experience on land experiments, that the spectral ratio models would be more robust (applicable to data collected from later dates) than the single band models. These expectations were proved correct, as shown in the next section.

The mathematical models for both LANDSAT 7 and LANDSAT 5 images were generated by using a step-wise linear regression method, with a Durbin-Watson statistical test for autocorrelation, which has been detailed by Vincent (2000). The Durbin-Watson (DW) test (Durbin and Watson, 1951) provided assurance that autocorrelation was not important in the parameters used for each final model reported. Although the DW test is more commonly employed in judging autocorrelation in multiple regression models of time series (multiple time inputs), it is equally useful for judging autocorrelation in regression models from multiple spectral band inputs. The test applies to regression models produced from any type of multiple inputs. The best model of each type of input (single bands and spectral ratios) was applied to the image the model came from, as well as to another image (with a different overpass date in year 2000), to test how well and how robustly each type of regression model performed.

The best PC and turbidity models were applied from Jul. 1, 2000 to LANDSAT 7 data collected on Jul. 16, 2002 and on Aug. 2, 2002 of the adjacent frame area to the East (P. 19, R. 31). It was later reported by local media that a *Microcystis* spp. bloom occurred in the western basin of Lake Erie late in the summer of 2002.

Results and Discussions

For the LANDSAT 7 image collected on Jul. 1, 2000, strong correlations were found for both the best single band model and the best spectral ratio model. The best single band model, which had an $R^2$ (Adjusted)=73.8% and a standard error of S=0.6402 micrograms/liter (about 16% of the total PC range for the Jul. 1, 2000 overpass), is given by the following equation for relative phycocyanin content:

$$PC = 0.78 - 0.0539(B1) + 0.176(B3) - 0.216(B5) + 0.117(B7) \quad \text{Eqn. 4}$$

where B1, B3, B5, and B7 stand for dark-object-subtracted digital numbers of LANDSAT TM band 1, band 3, band 5 and band 7, respectively.

In the preferred embodiment, the best spectral ratio model, which had an $R^2$ (Adjusted)=77.6% and S=0.5921 micrograms/liter (about 14.8% of the total PC range for the Jul. 1, 2000 overpass), is given by $$PC(\mu g/L) = 47.7 - 9.21(R31) + 29.7(R41) - 118(R43) - 6.81(R53) + 41.9(R73) - 14.7(R74) \quad \text{Eqn. 5}$$

wherein RIJ (formerly called $R_{i,j}$) stands for the dark-object-subtracted spectral ratio of the Ith band over the Jth band. Only the spectral ratio model definitively passed the DW test; the single band model was undetermined in the DW test. Predicted values by the single band model and the spectral ratio model of phycocyanin for the Jul. 1, 2000 overpass of LANDSAT 7 are plotted in FIG. 2 and FIG. 3, respectively, versus PC for each of the data collection sites in Lake Erie. The same two models were then applied to the LANDSAT 5 data obtained on Sep. 27, 2000. The spectral ratio model did reasonably well, as shown in FIG. 4, and the predictive error of PC from the L7 overpass model (Jul. 1, 2000) was 2.002 micrograms/liter for each value of PC measured in the L5 overpass (Sep. 27, 2000) water sample data set, or about 18.2% of the total range in PC for the Sep. 27, 2000 water samples. As shown in FIG. 5, the single band model produced worse results than did the spectral ratio model, proving that the best spectral ratio model is more robust than the best single band model with regard to changes in sun angle (season), atmospheric transmission, and instrument settings between these two overpasses of LANDSAT 7 (Jul. 1, 2000) and LANDSAT 5 (Sep. 27, 2000).

The same analysis (extracting the best single band combination model and the best spectral ratio model) was performed for the LANDSAT 5 data set, which had only 20 samples collected instead of the 30 for the LANDSAT 7 overpass. The regression model derived from spectral ratios passed the DW test [$R^2$(Adjusted)=63.2%, PC=16.9+58.3(R31)−108(R42)−31.5(R53)−1.63(R75)], but was not as strong as the LANDSAT 7 data set model, presumably because of the smaller sample size for the L5 overpass data set. The single band model was once again undetermined in the DW test.

Models for Chlorophyll a derived from both LANDSAT 7 and LANDSAT 5 datasets had high R-sqr values, but both of them failed to apply well to each other. While there was no reasonable model that could be obtained for the IVPF/IVCF ratio from the LANDSAT 7 dataset [$R^2$(Adj.)=35.5%], a strong correlation was found between this ratio and a spectral ratio derived from LANDSAT 5 dataset [$R^2$ (Adj.)=81.5%]. Application of this model to the LANDSAT 7 dataset generated a worse result. The possible reason for the poor performance of any model for the IVPF/IVCF ratio applied to the LANDSAT 7 data set is that the water sample obtained on Sep. 27, 2000 (a LANDSAT 5 overpass day) was highly dominated by cyanobacteria, as evidenced by the much higher IVPF/IVCF (>3.5) than that obtained from the Jul. 1, 2000 (LANDSAT 7) data set (<1.0).

The application of the best LANDSAT 7, Jul. 1, 2000 model for PC (using spectral ratios) to the LANDSAT 7 frame of Jul. 1, 2000 is shown in FIG. 6, where redder color in the water corresponds to higher amounts of PC (in micrograms/liter). FIG. 7 shows an image of the same LANDSAT 7, Jul. 1, 2000 spectral ratio PC model applied to the LANDSAT 5 frame of Sep. 27, 2000.

Note that there is much higher PC in the Sep. 27, 2000 image (FIG. 7) than in the Jul. 1, 2000 image (FIG. 6), which coincides with the expected temporal occurrence of blooms of *Microcystis* spp. that typically peak in Lake Erie in late September, for years in which they have been recorded to occur.

Although all 15 possible non-reciprocal (RJI was considered redundant to RIJ) spectral ratios underwent multiple regression analysis, the best spectral ratio model in Equation 5 employed only six ratios: R31, R41, R43, R53, R73, and R74. LANDSAT TM band 3 is in four of those spectral ratios. FIG. 8 (Green, 2003) shows reflectance spectra of water samples from two lakes, one of which contains predominantly chlorophyll a and the other of which contains both phycocyanin and chlorophyll a. Note that phycocyanin displays its most characteristic reflectance minimum within the wavelength limits of TM bands 2 and 3, but the gap between the two bands contains more phycocyanin absorption than either band 2 or 3. One of the spectral ratios in the PC algorithm (Equation 5) is R31, which is understandable because the average of both spectral curves in TM band 1 (see FIG. 8) are approximately equal, yet the reflectance is significantly higher for the lake water sample with little or no phycocyanin, compared to the one with elevated phycocyanin, in TM band 3. The other ratios all involve TM bands 4, 5, and 7, but neither of the spectra in FIG. 8 extends to those wavelengths. It seems reasonable, however, to assume that these reflective infrared bands are "sounding" near-surface water depths, at least in the top half-meter, as the extinction coefficients of water increase with increasing wavelength.

FIG. 9 is a plot of relative phycocyanin content and turbidity from the 30 water samples collected on Jul. 1, 2000, showing that the two parameters are somewhat correlated. Because of this, one may search for the best spectral ratio model for turbidity, as reported herein from the Jul. 1, 2000 water samples that passed the DW test, so that one may compare the turbidity and PC patterns in a body of water, as was done with respect to Lake Erie. In this example that search resulted in the following equation, with $R^2$ (Adj.) =85.2% and S=1.579 NTU (Nephlometric Turbidity Units), which is about 9% of the total turbidity range:

$$\text{Turbidity}(NTU) = -17.2 + 27.7(R32) \qquad \text{Eqn. 6}$$

Note from Equation 6 that this turbidity model includes only the R32 spectral ratio, which was not included in the PC algorithm of Equation 5. Muddy water has higher reflectance in the visible red (TM band 3) than the visible green (TM band 2) wavelength regions, so the fact that R32 is positively correlated with turbidity is not surprising. FIG. 10 shows actual versus predicted (Equation 6) turbidity for the Jul. 1, 2000 LANDSAT 7 frame.

This turbidity model may then be applied to a small portion of data, such as the Jul. 1, 2000 frame of LANDSAT ETM+ data, which is shown in FIG. 11 with the PC model image of the same area for comparison. The areas of highest PC occur in relatively high turbidity zones, but may not correspond with areas of highest turbidity, such as those which are in the Maumee River, upstream (SW) of the mouth. This, plus the fact that none of the ratios are repeated between Eqns. 5 and 6, are evidence that one may indeed map PC and turbidity separately, though the two parameters tend to be somewhat correlated in the original water samples.

The detection of algal pigmentation signatures from space by satellite remote sensing permits the present invention of large areas of aquatic systems synoptically. Guided by advances in pigment analysis, the compositions of algal populations in aquatic systems are theoretically detectable by remote sensing. To date, the application of remote sensing to aquatic systems has focused mainly on the detection of chlorophyll a (Abbot and Chelton, 1991; Smith and Baker, 1982), the pigment common to all phytoplankton. Several satellite-borne sensors have been used for this purpose, including Coastal Zone Color Scanner (CZCS), Airborne Ocean Color Imager (AOCI), SeaWiFS and Thematic Mapper (TM). The advantage of CZCS, AOCI, and SeaWIFS is that they have more spectral bands than TM and can probe the "gap" between the visible green and red bands (2 and 3) of TM. The advantages of LANDSAT TM over CZCS and SeaWiFS is that TM has a spatial resolution of 30 m, which is ideal for lakes and coastal zones that are difficult to study with the 1-kilometer spatial resolution of CZCS and SeaWiFS. In addition, TM has longer wavelength bands (5 and 7) extending to 2,350 nm wavelength.

Several groups have successfully used TM data for detection of phytoplankton (Galat and Verdin 1989, Gitelson et al. 1993, Richardson et al. 1991). LANDSAT has also been used to detect cyanobacterial blooms, albeit it on the basis of chl a distributions (Galat et al. 1990). As a result, that particular approach is of limited value, due to its inability to discriminate between phytoplankton groups. The present study is significant because it represents the first successful effort using LANDSAT TM to detect phycocyanin, a pigment specific to cyanobacteria as well as some cryptophytes. Until now, it was believed that the TM sensor was not suitable for detecting accessory pigments, including phycocyanin (with an absorption feature at 620 nm), because the TM bandwidths range from 20 nm to 80 nm. There have been several previous studies using hyperspectral sensors, such as AVIRIS and CAMS (both airborne sensors), to evaluate cyanobacterial populations (Millie et al. 1992; Richardson, 1996). The present findings have important implications for the future application of LANDSAT TM data on assessment and prediction of water quality of aquatic systems, not only by primary production estimates in which chlorophyll a serves as an important indicator, but also by the mapping of noxious cyanobacteria blooms in Lake Erie and other freshwater lakes and tributaries.

Another important finding of this study is that the model of the preferred embodiment derived from dark-object-subtracted spectral ratios is much more robust than any model one might derive from a combination of single spectral bands. The spectral ratio models obtained from both the LANDSAT 7 and the LANDSAT 5 data sets passed the DW test and could be applied to a data set collected at a different time with reasonable accuracy. In contrast, the single band models were undetermined in the DW test (meaning that there were auto-correlation problems) and these models could not be used accurately on a frame collected on another date. Therefore, the spectral ratio models were more robust than the single band combination models. This is a result that should hold regardless of the sensor data employed, not just to LANDSAT TM data, because it is based on the empirical removal of atmospheric haze prior to ratioing, which makes the spectral ratios directly proportional to the actual reflectance ratios of whatever the sensor is observing. If the reflectance spectrum is known for one area in the scene that does not change in time, such as the Marblehead quarry on the southern shore of Lake Erie in our case, the proportionality constants can also be determined and each ratio can be normalized for multiplicative changes in the ratios. In this experiment, this was not done, but that ratio normalization procedure would have improved the results in FIG. 4, making the PC model even more robust. The algorithm employed by Subramaniam et al (2001) for mapping *Trichodesmium* spp. in the ocean mixed the use of single bands and a ratio of two-band differences, which is not likely to be as robust as the dark-object-subtracted ratio algorithm produced by the method employed for phycocyanin in this investigation.

The phycocyanin model from Jul. 1, 2000 was then applied to a Jul. 16, 2002 LANDSAT 7 frame of the adjacent frame center (P. 19, R. 31) in our first attempt at employing the model to detect cyanobacterial blooms. The results of that experiment are shown in FIG. 12, with the color red corresponding to the highest levels of relative phycocyanin content. Note that the greatest concentrations of phycocyanin are indicated in Maumee Bay and north of Sandusky Bay, both in the western basin of Lake Erie, as well as along the northern shore of Lake St. Clair.

FIG. 13 shows the same type of image for a LANDSAT 7 overpass on Aug. 1, 2002. In both images, red corresponds to highest phycocyanin content (from 4.98-12.00 µg/L), which indicates that phycocyanin content in Lake Erie was greatly reduced on Aug. 1, 2002, compared with July 16, only sixteen days earlier. A synoptic survey of Maumee Bay conducted in the research boat on Aug. 1, 2002, however, indicated the presence of *Microcystis*, but the earlier Jul. 16, 2002 overpass had no corresponding validation of the presence of *Microcystis* or any other cyanophyte. The Aug. 1, 2002 sighting of *Microcystis* colonies floating at the surface amounted to about one or two colonies per square meter, a low count. FIG. 14 shows PC for an Aug. 8, 2002 LANDSAT 7 frame of Path 20, Row 31, with an optimal stretch of the image (red is 11.57-12.51 µg/L, orange is 10.25-11.57 µg/L, yellow is 8.00-10.25 µg/L, green is 5.62-8.00 µg/L and blue is 0-5.62 µg/L. If this image had the same stretch limits as FIGS. 2 and 13, all colors in the FIG. 14 image would have been red except for some of the dark blue pixels, indicating far more PC in westernmost Lake Erie than on either Jul. 16 or Aug. 1, 2002. There were no LANDSAT frames of P19R31 collected after Aug. 1, 2002 sufficiently cloud-free for PC analysis until December, 2002.

Local media reported on Sep. 17, 2002 that a substantial bloom of *Microcystis* had enveloped parts of the western basin in the vicinity of the Lake Erie islands (Toledo Blade, 2002). Although it is tempting to suggest an emergent *Microcystis* bloom on Jul. 16, 2002 was documented, the reduction in PC (as measured by the Jul. 1, 2000 PC model) evident on Aug. 1, 2002 does not support this. It is possible that the model was improperly implemented on the Aug. 1, 2002 frame, but those results have been checked and re-checked for that possibility and the implementation was found to be true. Alternatively, the variation in apparent PC levels may simply represent natural fluctuations in cyanophyte populations. Recently, Brunberg and Blomqvist (2003) reported such fluctuation in a pelagic population of *Microcystis* in a Swedish lake. The variation might also be the result of physical mixing that dispersed the population evident on Jul. 16, 2002 throughout the water column to depths inaccessible to detection by LANDSAT. Another possible natural explanation is that phycocyanin produced by organisms other than cyanobacteria were responsible for the higher PC content on Jul. 16, 2002, and the *Microcystis* bloom may not have occurred until August. Four genera of cryptophyte algae produce phycocyanin (Hill and Rowan, 1989; Deane et al. 2002), including one, *Chroomonas norstedtii*, that has been reported to occur in the western basin of Lake Erie (Makarewicz, 1993). Subsequent microscopic and lab analysis of water samples collected near July 16 indicated the presence of cryptophytes, although their specific identity was not determined. Thus, it is possible that a phycocyanin-containing cryptophyte was at least partially responsible for the phycocyanin signature observed on July 16 (FIG. 12). Similarly, single-celled cyanobacteria (such as *Synechoccus* sp. and *Synechocystis* sp.) could have provided the basis for the elevated phycocyanin signature, yet would not have been readily observed as part of routine microscopic examination of the water samples from that date.

In either case, it seems likely that at least the Aug. 8, 2002 image (FIG. 14) was the beginning of a large *Microcystis* bloom reported on September 17 in local media. However, the occurrence of a reduced PC content on Aug. 1, 2002, presents complications that may not allow one to detect early stage cyanobacterial blooms.

Since the extensive bloom of *Microcystis* in Lake Erie in 1995 (Brittain et al. 2000; Budd et al. 2002), researchers have continued to examine various potential bloom-causing conditions such as changes in nutrients, temperature, light levels, or even selective feeding—and subsequent rejection as pseudofaces by zebra mussels (Vanderploeg et al. 2001).

The present invention thus is a method that employs LANDSAT TM remote sensing technology for quantitatively mapping relative phycocyanin content of freshwater lakes from space or other remote locations. From water samples collected during two LANDSAT overpasses, a spectral ratio algorithm (Equation 5) for PC with a standard error of 0.592 µg/L (about 14.8% of the PC total range on Jul. 1, 2000) was created that predicted the PC values on a LANDSAT 5 overpass with an error of 2.00 µg/L (about 18.2% of the PC total range on Sep. 27, 2000). This error is sufficiently small to permit us to map large increases in PC that occur seasonally, and hence, to map cyanobacterial blooms, with the assumption that they also create differences in PC of similar or larger magnitude. Because the PC and turbidity data from the Jul. 1, 2000 water samples were somewhat correlated, we also created a turbidity model and showed that the highest PC values and the highest turbidity values did not coincide, though the highest PC values were found in relatively high turbidity areas. This, plus the non-overlap in spectral ratios employed by the PC and turbidity algorithms, provided evidence that we were mapping PC and turbidity separately. Thus, the concentration and spatial distribution of cyanobacteria can indeed be assessed by use of the LANDSAT TM sensor's six visible/reflective infrared spectral bands The second question was not completely answered by this investigation, though the Aug. 8, 2002 LANDSAT 7 frame for P20R31 (including the city of Toledo) showed a marked increase in PC (using the best Jul. 1, 2000, PC spectral ratio model) from both Jul. 16 and Aug. 1, 2002, and local media on Sep. 17, 2002 announced a major *Microcystis* bloom. The drop in PC content from Jul. 16 to Aug. 1, 2002 presents a complication that has yet to be resolved, though it could have been caused by phycocyanin from other phytoplankton (cryptophytes or other cyanobacteria) on Jul. 16, 2002, or as a result of natural fluctuations in a population of *Microcyctis*.

The present invention takes advantage of two technology-based approaches: the use of remote sensing, which quantitatively measures light reflected from the surface of the earth, as a tool to study regional-scale aquatic ecosystem dynamics, and the refinement of techniques to identify and quantify algal pigments (Richardson, 1996).

Accordingly, the findings from practice of the method of the present invention are as follows:

The LANDSAT TM sensor can be used to evaluate water quality by means of detecting accessory pigments of algae, such as phycocyanin, despite the relatively wide range of the sensor's spectral band width. Detection of phycocyanin may serve as a tool to detect and map cyanobacterial blooms, including blooms of the noxious *Microcystis*.

LANDSAT 7 and LANDSAT 5 datasets can be used together to enable a more timely assessment and early stage detection of noxious cyanobacterial blooms in Lake Erie by providing an 8-day monitoring interval instead of the 16-day interval that only one satellite provides.

Spectral ratio multiple regression models are more robust and reliable than single band multiple regression models for mapping relative phycocyanin content from LANDSAT TM data.

The 30-meter spatial resolution of LANDSAT TM bands 1-5 and 7, which were the only ones used in this experiment, is adequate to reach upstream into tributaries of Lake Erie for the measurement of PC and turbidity.

Mass blooms of cyanobacteria occur in freshwater and estuarine ecosystems throughout the world. These results, based on cyanobacteria in Lake Erie, show that one may employ the remote sensing technology to detect and map potential toxic cyanobacterial blooms elsewhere. It is believed that the method of the present invention will allow for the extraction of valuable information for assessment, monitoring, and early stage detection of cyanobacterial blooms, water quality, and aquatic ecosystem health from LANDSAT TM data on regional and global scales.

The present invention thus helps expand the understanding of the cyanobacterial bloom-forming process and its temporal/spatial distributions in Lake Erie and other systems. Further, one may gain a comprehensive understanding of the quantitative connections between algal accessory pigments, spectral signatures, and assessment of aquatic ecosystem function by the detection of pigments. The present invention may also provide an appropriate platform for further development, testing, and improvement of algorithms applied to monitor and predict water quality, which are analytically derived and have true multi-temporal robustness.

The color key for the total phycocyanin assay data shown in FIGS. 2-9, 14:

| Color | Colonies (Phycocyanin) per 100 MI of Water |
|---|---|
| Red | 14000-18300 |
| Orange | 10800-13900 |
| Yellow | 10200-10700 |
| Yellow-Green | 9600-10100 |
| Green | 7000-9000 |
| All Blues | 0-6900 |

Additional background for the invention is provided by the following references which are hereby incorporated by reference.

References

Abbott, M. R., Chelton, D. B. (1991). Advances in passive remote sensing of the ocean. Geophysics Supplement: 571-589.

Brittain, S. M., Wang, J., Babcock-Jackson, L., Carmichael, W. W., Rinehart, K. L., Culver, D. A., (2000). Isolation and characterization of microcystins, cyclic heptapeptide hepatotoxins from a Lake Erie strain of Microcystis aeruginosa. *Journal of Great Lakes Research*, 26, 241-249.

Brunberg, A.-K., Blomqvist, P. (2003). Recruitment of *Microcystis* (Cyanophyceae) from lake sediments: The importance of littoral inocula. *Journal of Phycology*, 39, 58-63.

Budd, J. W., Beeton, A. M., Stumpf, R. P., Culver, D. A., Kerfoot, W. C. (2002). Satellite observations of *Microcystis* blooms in western Lake Erie. *Verhandlungen Internationale Vereinigung fur theoretische und angewandte Limnologie*, 27, 3787-3793.

Carmichael, W. W. 2001. Health effects of toxin-producing cyanobacteria: "The CyanoHABs". *Human and Ecological. Risk Assessment*, 7, 1393-1407.

Cowles, T. J., Desiderio, R. A. and Neuer S. (1993). In situ characterization of phytoplankton from vertical profiles of fluorescence emission spectra. *Marine Biology*, 115, 217-222.

Deane, J. A., Strachan, I. M., Saunders, G. W., Hill, D. R. A., McFadden, G. I. (2002). Cryptomonad evolution: nuclear 18S rDNA phylogeny versus cell morphology and pigmentation. *Journal of Phycology*, 38, 1236-1244.

Dekker, A. G. (1993). Detection of optical water quality parameters for eutrophic waters by high resolution remote sensing. Ph.D Thesis, Free University, Amsterdam.

Durbin, J., and Watson, G. S. (1951). Testing for serial correlation in least squares regression. II. *Biometrica*, 38,159-178.

Falconer, I. R., Humpage, A. R. (1996). Tumour production by cyanobacterial toxins. *Phycologia*, 35 (6 Suppl), 74-79.

Galat, D. L, Verdin, J. P. (1989). Patchiness, collapse and succession of a cyanobacterial bloom evaluated by synoptic sampling and remote sensing. *Journal of Plankton Research*, 11, 925-948.

Galat, D. L., Verdin, J. P., Sims, L. L. (1990). Large-scale patterns of *Nodularia spumigena* blooms in Pyramid Lake, Nevada, determined from Landsat imagery: 1972-1986. *Hydrobiologia*, 197, 147-164.

Gitelson, A., Garbuzov, G., Szilagyi, F., Mittenzwey, K. H., Karnieli, A., Kaiser, A. (1993). Quantitative remote sensing methods for real-time monitoring of inland waters quality. *International Journal of Remote Sensing*, 14, 1269-1295.

Green, S., 2003, http://www.ucd.ie/~app-phys/stuart/MODEL.HTM, The Effect of Chlorophyll Concentration on Airborne Hyperspectral Reflectance.

Hill, D. R. A., Rowan, K. S. (1989). The biliproteins of the Cryptophyceae. *Phycologia*, 28, 455-463.

Lake Erie LaMP (2002). The Lake Erie Lakewide Management Plan. J. Letterhos and J. Vincent (Eds.), Environment Canada, Ontario Region and U.S. Environmental Protection Agency, Region 5.

MacColl, R., Guard-Friae, D. (1987). *Phycobiliproteins*. Boca Raton, Fla.: CRC Press Makarewicz, J. C. (1993). Phytoplankton biomass and species composition in Lake Erie, 1970 to 1987. *Journal of Great Lakes Research*, 19, 258-274.

Millie, D. F., Baker, M. C., Tucker, C. S., Vinyard, B. T., Dionigi, C. P. (1992). High-resolution airborne remote sensing of bloom-forming phytoplankton. *Journal of Phycology*, 28, 281-290.

Richardson, L. L, Bachoon, D., Ingram-Willey, V., Chee, Chow C., Weinstock, K. (1991). Remote sensing of the biological dynamics of large-scale salt evaporation ponds. Pages 611-623 in Proceedings of the International Symposium on Remote Sensing of Environment; 27-31 May; Rio de Janeiro, Brazi.

Richardson, L. L. (1996). Remote sensing of algal bloom dynamics. *BioScience*, 44, 492-501.

Rowan, K. S. (1989). *Photosynthetic pigments of algae*. Cambridge University Press.

Smith, R. C., Baker, K. S. (1982). Oceanic chlorophyll concentrations as determined by satellite (Nimbus-7 Coastal Zone Color Scanner). *Marine Biology*, 66, 269-279.

Subramaniam, A., Brown, C. W. Hood, R. R. Carpenter, E. J. and Capone, D. G. (2001). Detecting *Trichodesmium* blooms in SeaWiFS imagery. *Deep-Sea Research II*, 49(1-3),107-121.

Taylor, R. (1997). That bloomin' *Microcystis*: Where'd it come from? Where'd it go? *Twine Line*, 19, 1.

Toledo Blade, (2002). Toxic Algae Thrive in Summer's Heat, Article ID: 0209170185, Published on Sep. 17, 2002, The Blade, Toledo, Ohio.

Vanderploeg, H. A., Liebig, J. R., Carmichael, W. W., Agy, M. A., Johengen, T. H., Fahnenstiel, G. L., Nalepa, T. F. (2001). Zebra mussel (Dreissena polymorpha) selective filtration promoted toxic *Microcystis* blooms in Saginaw Bay (Lake Huron) and Lake Erie. *Canadian Journal of Fisheries and Aquatic Science*, 58, 1208-1221.

Vincent, R. K. (1997). *Fundamentals of Geological and Environmental Remote Sensing* (pp. 102-108). Upper Saddle River, N.J.: Prentice Hall.

Vincent, R. K. (2000). Forecasts of monthly averaged daily temperature highs in Bowling Green, Ohio from monthly sea surface temperature anomalies in the Eastern Pacific ocean during the previous year. *Photogrammetric Engineering & Remote Sensing*, 66(8), 1001-1009.

Watras, C. J., Baker, A. L. (1988). Detection of planktonic cyanobacteria by tandem in vivo fluorometry. *Hydrobiologia*, 169, 77-84.

Welschmeyer, N. A. (1994). Fluorometric analysis of chlorophyll a in the presence of chlorophyll b and pheopigments. *Limnology and Oceanography*, 41, 1425-1437.

Having shown and described a preferred embodiment of the invention, those skilled in the art will realize that many variations and modifications may be made to affect the described invention and still be within the scope of the claimed invention. Thus, many of the elements indicated above may be altered or replaced by different elements which will provide the same result and fall within the spirit of the claimed invention. It is the intention, therefore, to limit the invention only as indicated by the scope of the claims.

What is claimed is:

1. A method of determining the amount of phycocyanin-pigmented algae or bacteria in water from light reflected therefrom, said method comprising the steps of:
   (a) obtaining a measurement of reflected light from said water, using a light measurement device, said measurement comprising a measurement of the respective amounts of light in at least two of the following wavelength ranges: (i) from about 0.45 μm to about 0.52 μm (ii) from about 0.63 μm to about 0.69 μm; (iii) from about 0.76 μm to about 0.90 μm; (iv) from about 1.55 μm to about 1.75 μm and (v) from about 2.08 μm to about 2.35 μm; and
   (b) determining the amount of said phycocyanin-pigmented algae or bacteria in said water from said respective amounts of light by applying an algorithm, using a microprocessor, relating said respective amounts of light in said at least two of said wavelength ranges to said amount of said phycocyanin-pigmented algae or bacteria in said water, and wherein said algorithm comprises a quantitative relationship between the ratio of the amount of light in a first of said wavelength ranges to the amount of light in a second of said wavelength ranges, and the amount of said phycocyanin-pigmented algae or bacteria in said water.

2. A method according to claim 1 wherein said light measurement device is selected from the group consisting of a photosensor, camera, digital camera and video camera.

3. A method according to claim 1 wherein the calculated value of said amount of phycocyanin-pigmented algae or bacteria correlates to the actual measured amount of said phycocyanin-pigmented algae or bacteria in said water by a correlation value in excess of 60%.

4. A method according to claim 1 wherein the calculated value of said amount of phycocyanin-pigmented algae or bacteria correlates to the actual measured amount of said phycocyanin-pigmented algae or bacteria in said water by a correlation value in excess of 80%.

5. A method of determining the amount of phycocyanin-pigmented algae or bacteria in water from light reflected therefrom, said method comprising the steps of:
   (a) obtaining a measurement of reflected light from said water, using a light measurement device, said measurement comprising a measurement of the respective amounts of light at three wavelengths; and
   (b) determining the amount of said phycocyanin-pigmented algae or bacteria in said water from said respective amounts of light by applying an algorithm, using a microprocessor, relating said respective amounts of light in said three wavelengths to said amount of said phycocyanin-pigmented algae or bacteria in said water, wherein said algorithm comprises a quantitative relationship between the sum of (1) the ratio of the amount of light at the first of said wavelengths to the amount of light at the second of said wavelengths and (2) the ratio of the amount of light at the second of said wavelengths to the amount of light at the third of said wavelengths; and the amount of said phycocyanin-pigmented algae or bacteria in said water.

6. A method according to claim 5 wherein said light measurement device is selected from the group consisting of a photosensor, camera, digital camera and video camera.

7. A method according to claim 5 wherein the calculated value of said amount of phycocyanin-pigmented algae or bacteria correlates to the actual measured amount of said phycocyanin-pigmented algae or bacteria in said water by a correlation value in excess of 60%.

8. A method according to claim 5 wherein the calculated value of said amount of phycocyanin-pigmented algae or bacteria correlates to the actual measured amount of said phycocyanin-pigmented algae or bacteria in said water by a correlation value in excess of 80%.

9. A method of determining the amount of phycocyanin-pigmented algae or bacteria in water from light reflected therefrom, said method comprising the steps of:
   (a) obtaining a measurement of reflected light from said water, using a light measurement device, said measurement comprising a measurement of the respective amounts of light in at least two wavelengths within respective two of the following five wavelength ranges: (i) from about 0.45 μm to about 0.52 μm (ii) from about 0.63 μm to about 0.69 μm; (iii) from about 0.76 μm to about 0.90 μm; (iv) from about 1.55 μm to about 1.75 μm and (v) from about 2.08 μm to about 2.35 μm; and
   (b) determining the amount of said phycocyanin-pigmented algae or bacteria in said water from said respective amounts of light by applying an algorithm, using a microprocessor, relating said respective amounts of light in said at least two wavelengths to said amount of said phycocyanin-pigmented algae or bacteria in said water, wherein said algorithm comprises a quantitative relationship between the ratio of the amounts of light at the first of said wavelengths to the amounts of light at the second of said wavelengths and the amount of said phycocyanin-pigmented algae or bacteria in said water.

10. A method according to claim 9 wherein said algorithm comprises a measurement of the respective amounts of light in: (i) LANDSAT TM band 1, (ii) LANDSAT TM band 3, (iii) LANDSAT TM band 4, and (iv) LANDSAT TM band 5, and wherein said algorithm comprises a quantitative relationship between the sum of the following ratios:
   (a) the reflectance in LANDSAT TM band 3 divided by the reflectance in LANDSAT TM band 1, after subtraction of the reflectance of atmospheric haze separately in each band;
   (b) the reflectance in LANDSAT TM band 4 divided by the reflectance in LANDSAT TM band 1, after subtraction of the reflectance of atmospheric haze separately in each band;
   (c) the reflectance in LANDSAT TM band 4 divided by the reflectance in LANDSAT TM band 3, after subtraction of the reflectance of atmospheric haze separately in each band; and
   (d) the reflectance in LANDSAT TM band 5 divided by the reflectance in LANDSAT TM band 3, after subtraction of the reflectance of atmospheric haze separately in each band.

11. A method according to claim 9 wherein said light measurement device is selected from the group consisting of a photosensor, camera, digital camera and video camera.

12. A method according to claim 9 wherein the calculated value of said amount of phycocyanin-pigmented algae or bacteria correlates to the actual measured amount of said phycocyanin-pigmented algae or bacteria in said water by a correlation value in excess of 60%.

13. A method according to claim 9 wherein the calculated value of said amount of phycocyanin-pigmented algae or bacteria correlates to the actual measured amount of said phycocyanin-pigmented algae or bacteria in said water by a correlation value in excess of 80%.

* * * * *